United States Patent
Wells

(10) Patent No.: US 10,912,911 B2
(45) Date of Patent: Feb. 9, 2021

(54) DEVICE FOR SECURING A NASAL CANNULA

(71) Applicant: Noel E. Wells, Cape Canaveral, FL (US)

(72) Inventor: Noel E. Wells, Cape Canaveral, FL (US)

( * ) Notice: Subject to any disclaimer, the term of this patent is extended or adjusted under 35 U.S.C. 154(b) by 0 days.

(21) Appl. No.: 16/244,605

(22) Filed: Jan. 10, 2019

(65) Prior Publication Data

US 2019/0143067 A1    May 16, 2019

Related U.S. Application Data

(63) Continuation-in-part of application No. 16/113,298, filed on Aug. 27, 2018, which is a continuation-in-part of application No. 16/008,718, filed on Jun. 14, 2018, now Pat. No. 10,434,274.

(60) Provisional application No. 62/520,222, filed on Jun. 15, 2017.

(51) Int. Cl.
*A61M 16/06*    (2006.01)

(52) U.S. Cl.
CPC .... *A61M 16/0688* (2014.02); *A61M 16/0672* (2014.02); *A61M 2202/0208* (2013.01); *A61M 2209/088* (2013.01); *A61M 2210/0618* (2013.01)

(58) Field of Classification Search
CPC .......... A61M 16/0688; A61M 16/0672; A61M 2202/0208; A61M 2209/088; A61M 2210/0618
See application file for complete search history.

(56) References Cited

U.S. PATENT DOCUMENTS

| | | | |
|---|---|---|---|
| 2,526,586 A | 10/1950 | Shuff | |
| 4,378,802 A | 4/1983 | Ersek | |
| 4,707,906 A | 11/1987 | Posey | |
| 5,113,857 A | 5/1992 | Dickerman et al. | |
| 5,117,818 A | 6/1992 | Palfy | |
| 5,752,511 A | 5/1998 | Simmons et al. | |
| 5,946,778 A | 9/1999 | McGarity | |
| 6,328,038 B1 * | 12/2001 | Kessler | A61M 16/0666 128/200.25 |
| 6,804,866 B2 | 10/2004 | Lemke et al. | |
| 6,981,569 B2 | 1/2006 | Stilp | |
| 7,024,235 B2 | 4/2006 | Melker et al. | |
| 7,108,198 B2 | 9/2006 | Altadonna, Jr. | |
| 7,614,401 B2 | 11/2009 | Thompson | |

(Continued)

OTHER PUBLICATIONS

A-M Systems: Nose Clip (Foam); Rubber and Foam Nose Clips for PFT; Sep. 23, 2014; http://www.a-msystems.comp/p-895-nose-clip-foam.aspx.

(Continued)

*Primary Examiner* — Timothy A Stanis
(74) *Attorney, Agent, or Firm* — Allen Dyer Doppelt & Gilchrist, PA

(57) ABSTRACT

A device for securing a nasal cannula to a patient includes a first adhesive strip configured to be releasably attached to columella of a nasal septum and a second adhesive strip configured to be releasbly attached to upper lip of the patient. The device further includes a clip connected to an elongated base member connecting the first and second adhesive strip, and the clip has an opening configured to secure the device to an oxygen tube of the nasal cannula.

1 Claim, 18 Drawing Sheets

(56) References Cited

U.S. PATENT DOCUMENTS

| | | | |
|---|---|---|---|
| 8,302,607 | B2 | 11/2012 | Pierce et al. |
| 9,730,830 | B2 | 8/2017 | Foley et al. |
| 9,795,770 | B1 | 10/2017 | Zolli |
| 9,867,553 | B2 | 1/2018 | Garayochea |
| 9,913,682 | B2 | 3/2018 | Wolf et al. |
| 9,981,101 | B2 | 5/2018 | VanMiddendorp et al. |
| 2002/0066452 | A1 | 6/2002 | Kessler et al. |
| 2002/0112730 | A1 | 8/2002 | Dutkiewicz |
| 2003/0236480 | A1* | 12/2003 | Landis ............... A61F 5/08 602/54 |
| 2008/0121230 | A1 | 5/2008 | Cortez |
| 2008/0216838 | A1 | 9/2008 | Wondka |
| 2010/0294271 | A1 | 11/2010 | Pittaway et al. |
| 2011/0125052 | A1 | 5/2011 | Davenport et al. |
| 2011/0218451 | A1 | 9/2011 | Lai et al. |
| 2011/0253136 | A1 | 10/2011 | Sweeney et al. |
| 2012/0111340 | A1 | 5/2012 | Robitaille |
| 2012/0167894 | A1* | 7/2012 | O'Leary ............ A61M 16/0666 128/207.18 |
| 2012/0232490 | A1* | 9/2012 | Andino ............... A61M 25/02 604/180 |
| 2015/0090255 | A1* | 4/2015 | Gulliver ............ A61M 16/0688 128/202.15 |
| 2016/0235938 | A1 | 8/2016 | Khabiri et al. |

OTHER PUBLICATIONS

PCT International Searcing Authority; International Search Report and Written Opinion dated Oct. 18, 2018; entire document.

* cited by examiner

DEVICE FOR SECURING A NASAL CANNULA

CROSS-REFERENCE TO RELATED APPLICATION

This application is a continuation-in-part of U.S. Non-provisional patent application Ser. No. 16/113,298, filed on Aug. 27, 2018, which is a continuation-in-part of U.S. Non-provisional patent application Ser. No. 16/008,718, filed on Jun. 14, 2018, and which claims the benefit of U.S. Provisional Patent Application Ser. No. 62/520,222 filed on Jun. 15, 2017, the contents of which applications are herein incorporated by reference in their entirety.

FIELD OF THE INVENTION

The present invention generally relates to a device for securing a nasal cannula to a patient, and more particularly, to a device for securing a nasal cannula that provides secure and comfortable attachment to a patient.

BACKGROUND OF THE INVENTION

A nasal cannula is a device used to deliver oxygen or airflow to a patient for respiration. A portable oxygen generator or a wall connection in a hospital is used to supply the oxygen to the patient using the nasal cannula. The nasal cannula generally consists of a lightweight plastic tube that has two nasal prongs that fit inside the nostrils of the patient. The nasal cannula is always looped behind the patient's ears. A mixture of air and oxygen can flow directly to the patient's respiratory system when the nasal cannula is securely in place.

A nasal cannula is often times secured to the patient by taping it to the patient's cheekbones and looping the tube around the patient's ears or by using an elastic head band or other securing methods. Still, the nasal cannula is susceptible to accidental dislodging from the nostrils, for example, in patient movement and especially during sleep, unconscious movement or involuntary movement. There has therefore been a long-standing need to improve methods of securing a nasal cannula. Despite significant recent advancements in this area, further improvements are possible.

SUMMARY OF THE INVENTION

In view of the foregoing, it is an object of the present invention to provide a device to secure a nasal cannula to a patient. According to one embodiment of the present invention, the device includes a pair of opposing legs having a predefined opening therebetween and a clip secured to an opposite end of the pair of opposing legs. The clip has an opening configured to receive and secure the device to a tube. The pair of opposing legs are configured to slide over a nasal septum and are biased together to provide compression as the pair of legs are moved apart when sliding over the nasal septum.

According to another embodiment of the present invention, a method of securing an oxygen tube to a patient using a device for securing nasal cannula to a patient includes securing an oxygen tube to the clip of the device and sliding a pair of opposing legs over a nasal septum of the patient such that the predefined opening of the pair of opposing legs is biased together to provide compression again the nasal septum.

According to another embodiment of the present invention, a device for securing a nasal cannula to a patient includes an adhesive strip configured to be releasably attached to the columella of the nasal septum and a clip secured to the adhesive strip. The clip has an opening configured to secure the device to an oxygen tube.

According to yet another embodiment of the present invention, a method of securing an oxygen tube to a patient using a device for securing nasal cannula to a patient includes securing an oxygen tube to the clip of the device and attaching the adhesive strip of the device to the columella of the nasal septum.

According to yet another embodiment of the present invention, a device for securing a nasal cannula to a patient includes a first adhesive strip configured to be releasably attached to columella of a nasal septum and a second adhesive strip configured to be releasbly attached to upper lip of the patient. The device further includes a clip connected to an elongated member connected between the first and second adhesive strip, wherein the clip has an opening configured to secure the device to an oxygen tube of the nasal cannula.

According to yet another embodiment of the present invention, a method of securing an oxygen tube to a patient using a device for securing nasal cannula to a patient includes securing the oxygen tube to the clip of the device and attaching the first adhesive strip to the columella of the nasal septum. The second adhesive strip is then attached to the upper lip surface of the patient.

According to another embodiment of the present invention, a device for securing a nasal cannula to a patient a first adhesive strip configured to be releasably attached to columella of a nasal septum and a second adhesive strip configured to be releasbly attached to upper lip of the patient. The second adhesive strip includes an elongated opening. A clip is slidably connected to the second adhesive strip via the elongated opening, and the clip is configured to slide along the elongated opening to a desired position. The clip has an opening configured to secure the device to an oxygen tube of the nasal cannula.

According to another embodiment of the present invention, a device for securing a nasal cannula to a patient includes an adhesive strip configured to be releasbly attached to upper lip of the patient. The adhesive strip includes an elongated opening. A clip is slidably connected to the second adhesive strip via the elongated opening, and the clip is configured to slide along the elongated opening to a desired position. The clip has an opening configured to secure the device to an oxygen tube of the nasal cannula.

These and other objects, aspects and advantages of the present invention will be better appreciated in view of the drawings and following detailed description of preferred embodiments.

BRIEF DESCRIPTION OF THE DRAWINGS

Features and benefits of the present invention will become apparent as the description proceeds when taken in conjunction with the accompanying drawings in which.

DETAILED DESCRIPTION OF PREFERRED EMBODIMENTS

The present invention will now be described more fully hereinafter with reference to the accompanying drawings, in which various embodiments of the invention are shown. This invention may, however, be embodied in many different forms and should not be construed as limited to the embodiments set forth herein. Rather, these embodiments are provided so that this disclosure will be thorough and complete, and fully convey the scope of the invention to those skilled in the art. Like numbers refer to like elements throughout.

Figure 1:
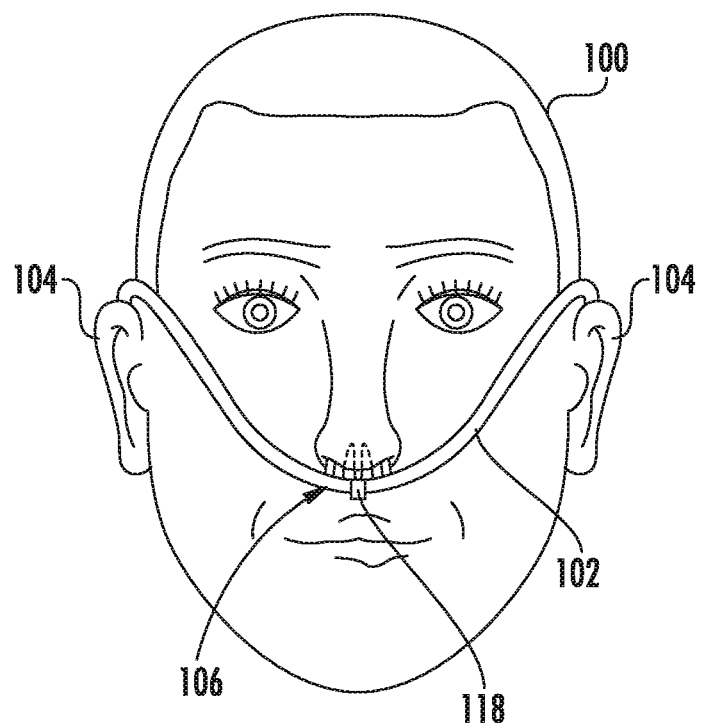
FIG. 1 is a front view of a particular illustrative embodiment of a device to secure a nasal cannula to a patient.
Figure 2:
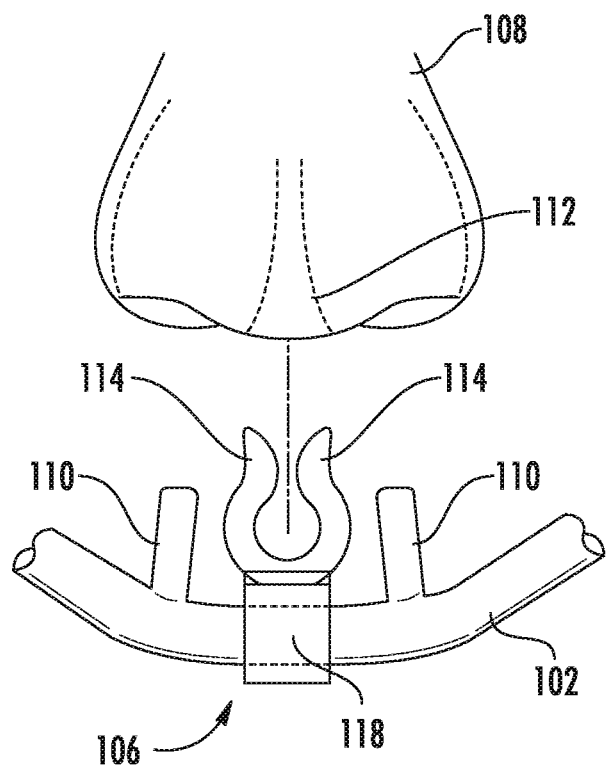
FIG. 2 is a detailed view of the apparatus clipped to an air tube, illustrating the relationship of the device and the nasal cannula to the patient.
Figure 3:
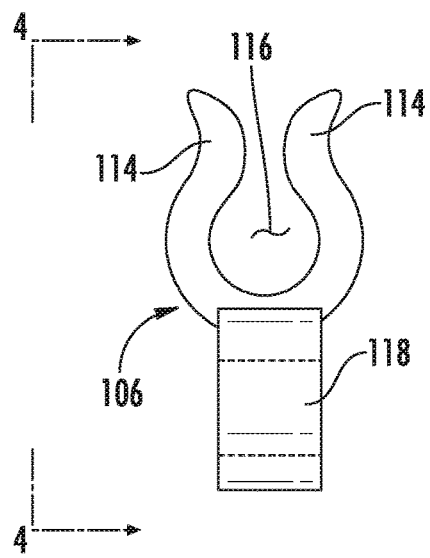
FIG. 3 is a front view of the device of FIGS. 1 and 2.

Referring now to FIGS. 1-3, a patient 100 typically receives oxygen through a continuous tube 102 that loops behind the ears 104 of the patient 100. Nasal cannula prongs 110 are formed or secured to the tube 102 and adapted to slide into the nostrils of the patient to supply oxygen. Oxygen travels through the tube 102 and is inhaled by the patient 100 through the nose 108.

The device 106 is used to secure the nasal cannula prongs 110 within the nose 108 of the patient 100. For example, an upper portion of the device 106 includes a pair of opposing legs 114 that are configured to slide over the nasal septum 112 of the patient 100 and uses a friction fit to hold the device 106 in place. The opposing legs 114 are biased to provide compression as the legs 114 are slightly moved apart when sliding over the nasal septum 112. A width 116 between the legs 114 may vary depending on the patient 100, but the width 116 must be smaller than the width of the nasal septum 112. For example, a small width 116 between the legs 114 is required a proper fit over the nasal septum 112 of a child, and a larger width 116 is required for adults. The upper portion of the device 106 may be U-shaped with rounded edges and corners to minimize any discomfort to the patient 100. In addition, gel pads or other cushioning material may be secured to an inside portion of the legs 114 to soften the contact area of the device 106 to the nasal septum 112. For example, the pair of opposing legs 114 are flexible and the distance between the opposing legs 114 can be adjusted. A pair of gel pads are attached at the end of opposing legs 114. The pair of opposing legs 114 can be inserted to the nostril and the pair of gel pads are attached to the inner surface of the nostril. This will improve the comfortability of the patient and the pair of gel pads can push the nostril inner surface and make the nostril cavity a little wider to facilitate easier breathing for the patient.

Figure 4:
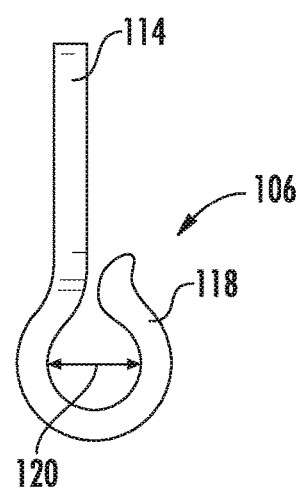
FIG. 4 is a side view of the device taken in the direction of line 4-4.

Referring now to FIG. 4, the device 106 includes a clip 118 that is configured to secure the device 106 to the tube 102. In this particular illustrative embodiment, the clip 118 is hook-shaped with an inside diameter 120 large enough to fit around an outside diameter of the tube 102 without interfering with the flow of oxygen through the tube 102, but small enough to provide a friction fit between the clip 118 and the tube 102. The clip 118 is made of the relatively elastic material being looped over itself to accommodate the oxygen delivery tube 102. The clip 118 has an opening 120 for receiving the oxygen delivery tube 102. More than one hook can be used. For example, the clip 118 can include two hooks in parallel with each other.

Figure 5:
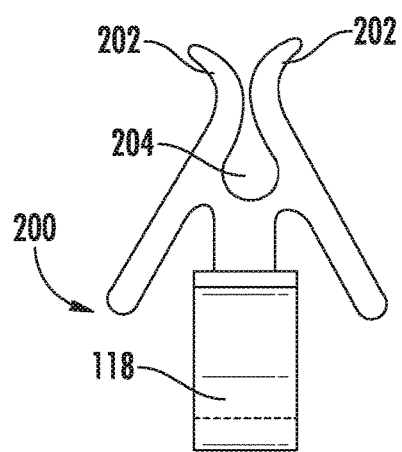
FIG. 5 is a front view of an alternative embodiment of the device to secure a nasal cannula to a patient.
Figure 6:
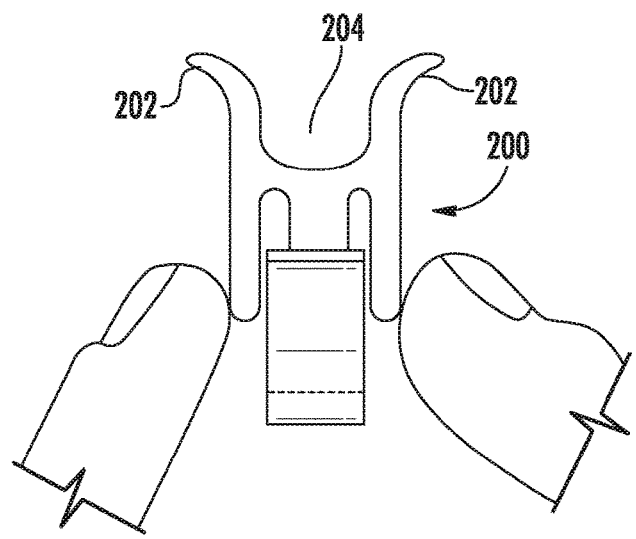
FIG. 6 is a front view of the device of FIG. 5, illustrating the device being manipulated.
Figure 7:
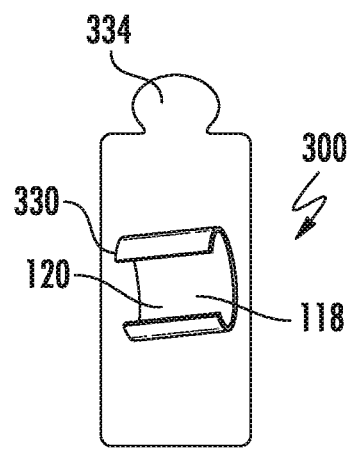
FIG. 7 is a bottom view of another alternative embodiment of the device to secure a nasal cannula to a patient.
Figure 8:
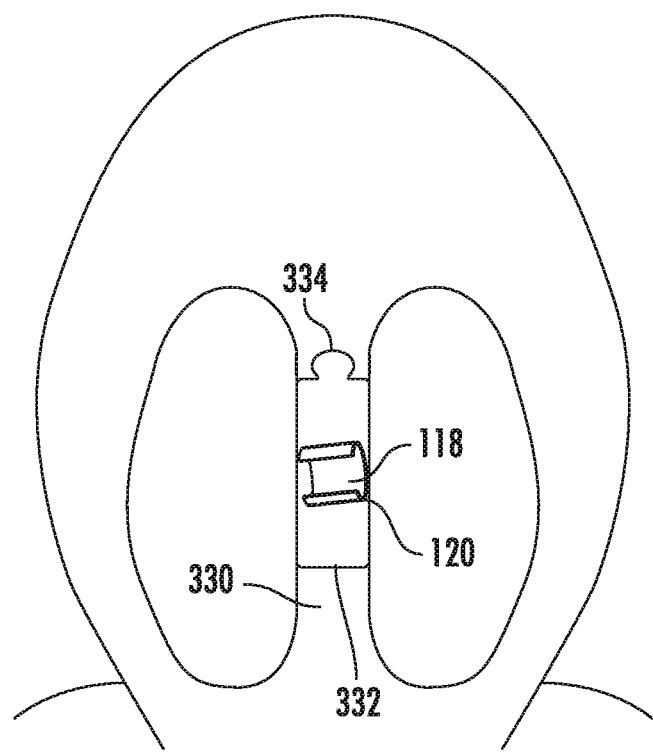
FIG. 8 is a bottom view of the device of FIG. 7, attached to the nasal septum of a patient.
Figure 9:
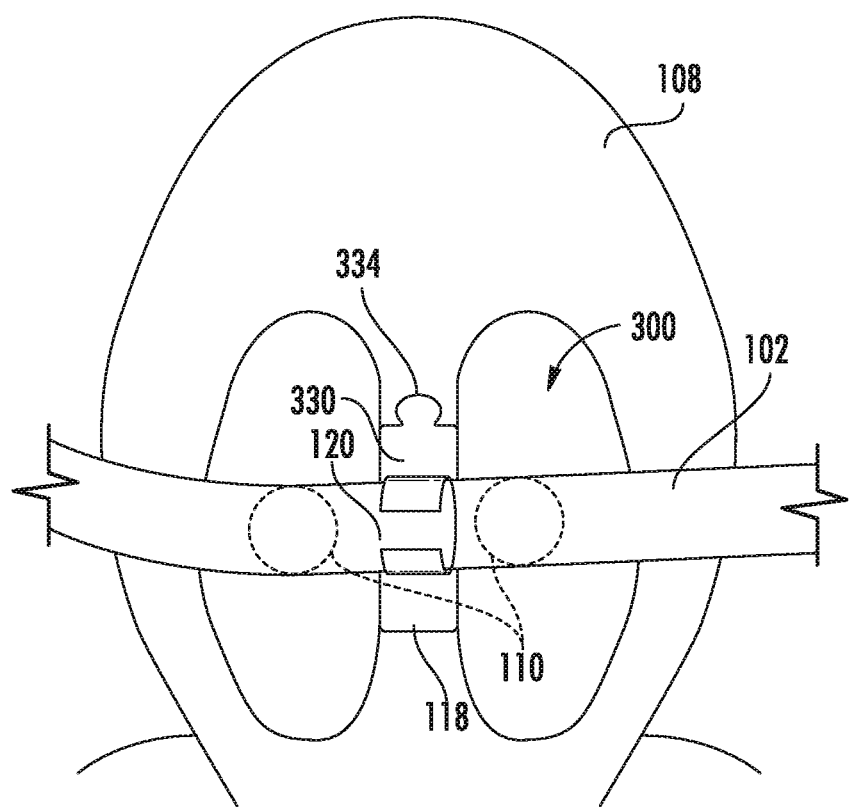
FIG. 9 is a bottom view of the device of FIG. 7, attached to the nasal septum of a patient and clipped to an air tube with nasal cannula.
Figure 10:
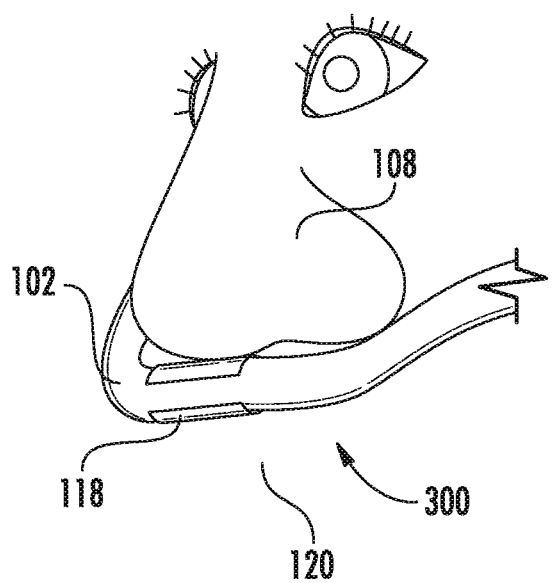
FIG. 10 is a perspective view of the device of FIG. 7, securing the air tube and nasal cannula to the nasal septum of a patient.

Referring now to FIGS. 5 and 6, an alternative illustrative embodiment is shown. The alternative device 200 similarly includes the clip 118 to secure the alternative device 200 to the tube 102 but has a different configuration to secure the alternative device 200 to the nasal septum 112. For example, prongs 202 of the alternative device 200 are biased and configured so that they can be manipulated by pinching the proximate ends. As shown in FIG. 6, as the proximate ends of the prongs 202 are pressed together and pressure is applied, the opposing distal ends of the prongs 202 move further apart about a fulcrum location. This manipulation allows the prongs 202 to slide over the nasal septum 112 without requiring tissue of the nasal septum to spread the prongs. Accordingly, once the alternative device 200 is in the desired location, the pressure on the proximate ends of the prongs 202 can be released, causing the distal ends of the prongs 202 to move closer together and remain securely to the nasal septum 112, as the width 204 between the prongs 202 is less than a width of the nasal septum 112. Accordingly, once the device 200 is in the desired location, the pressure on the proximate ends of the prongs 202 is released causing the distal ends of the prongs to move closer together and remain securely to the nasal septum.

Alternately, referring to FIGS. 7-10, the pair of legs/prongs can be eliminated altogether. In a device 300, a clip 118 is secured to an adhesive strip 330 which adheres to the columella 332 (i.e., the fleshy external termination) of the nasal septum 112. The adhesive strip 330 can use medical grade adhesive to hold the strip in place. If needed, additional medical adhesive can be applied to the strip prior to placing it on the columella 332 for extra strength. The strip 330 can be square, circular or any other shape suitable for attaching to the columella 332. An example dimension of the strip is about 0.64 centimeters in width and about 1.3 centimeters in length. Other dimensions can be used to accommodate a patient. The strip 330 can also have a curved support base. The curvature can facilitate placing the strip 330 on the columella 332 more easily and also help to center the strip 330 to the columella 332.

The clip 118 can be secured to the strip 330 via a hook-and-loop-type of fastener or another suitable fastener. The clip 118 can be permanently or releasably secured to the adhesive strip 330. In the releasable attachment, the clip 118 can be easily removed and/or reattached to the adhesive strip 330, for example, via attraction of magnets having opposite poles. For example, each of the adhesive strip 330 and the clip 118 can be attached to a magnet respectfully having opposite poles. The attraction of opposite poles of the respective magnet therefore can hold the strip 330 and the clip 118 together.

The clip 118 can be rotated relative to the adhesive strip 330 such that the opening 120 is pointed at a certain orientation or otherwise desired by a user to achieve a higher comfort level. The clip 118 has an opening 120 for receiving the oxygen delivery tube 102. The clip 118 is made of a relatively elastic material to receive the oxygen delivery tube 102 and accommodate the oxygen delivery tube 102. Preferably, a non-adhesive pull tab 334 is located at one end of the strip to facilitate removal. With the tube 102 secured to the clip 118 and the strip adhered to the columella 332, the cannula prongs 110 extend securely into the nose 108. The strip 330 can be applied to the columella 332 before or after securing the tube 102 to the clip 118. When it is desired to remove the device 300, the tab 334 is grasped and the strip 330 is removed from the columella 332. The tube 102 could, if desired, be removed from the clip 118 prior to or after removal of the strip 330 from the columella 332.

According to another embodiment of the present invention, a method of securing an oxygen tube to a patient includes using the device 300 securing an oxygen tube to the clip (e.g., clip 118) of the device 300 and attaching the adhesive strip (e.g., adhesive strip 330) to the columella of the nasal septum. Alternatively or additionally, the adhesive strip 330 can also be attached to the skin between upper lip and nose instead of columella 332.

Figure 11:
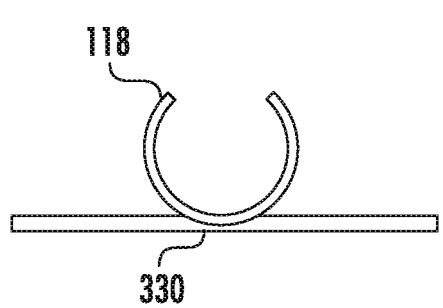
FIG. 11 is a front view of the device of FIG. 7, employing an extension member, the extension member being in a retracted position.
Figure 12:
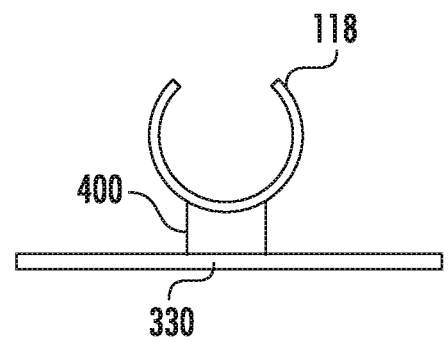
FIG. 12 is a front view of the device of FIG. 7, employing an extension member, the extension member being in a partially extended position.
Figure 13:
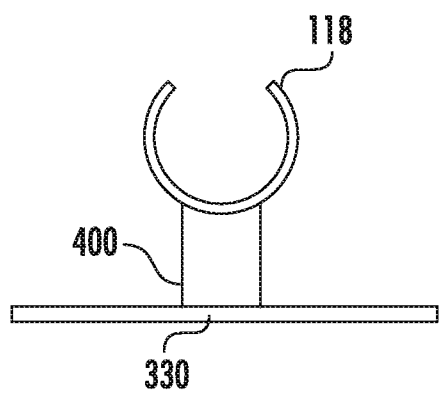
FIG. 13 is a front view of the device of FIG. 7, employing an extension member, the extension member being in a fully extended position.

According to another embodiment of the present invention, an extension member 400 can be mounted between the clip 118 and the adhesive strip 330 of FIGS. 7-10 or between the clip 118 and the pair of opposing legs 114. For example, as shown in FIGS. 11-13, the extension member 400 can be in a retracted state as shown in FIG. 11, a partially extended state as shown in FIG. 12, or a fully extended state as shown in FIG. 13 to achieve a desired length for a user. The extension member 400 can introduce a distance between the clip 118 and the pair of opposing legs 114 or between and the clip 118 and the adhesive strip 330. In a preferred embodiment, the cross section of the end of the extension member 400 attaching to the adhesive strip 330 is greater than the cross section of the end of the extension member 400 attaching to the clip 118 to provide more stability. A desired placement of the air delivery prongs relative to the oxygen delivery tube 102 can thus be achieved. For example, the extended extension member 400 can result in the air delivery prongs being just inside or just outside of nostrils such that an oxygen delivery tube (e.g., oxygen delivery tube 102) has no contact with patient's nostrils and irritation from contact is minimized. For example, the extension member 400 can be designed as a plurality of slidable sections in a telescoping arrangement.

Figure 14:
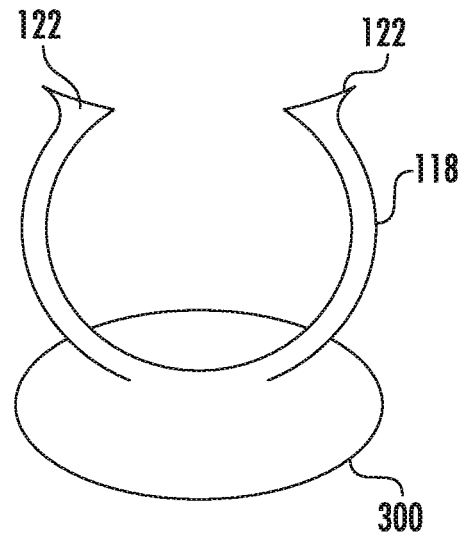
FIG. 14 is a front view of a clip secured to an adhesive clip, according to another embodiment of the present invention.

Referring to FIG. 14, according to another embodiment of the invention, the clip 118 of the devices described in FIGS. 1-13 can include appendages 122 on the respective ends to facilitate securing the oxygen tube (not shown) inside the clip 118.

Figure 15:
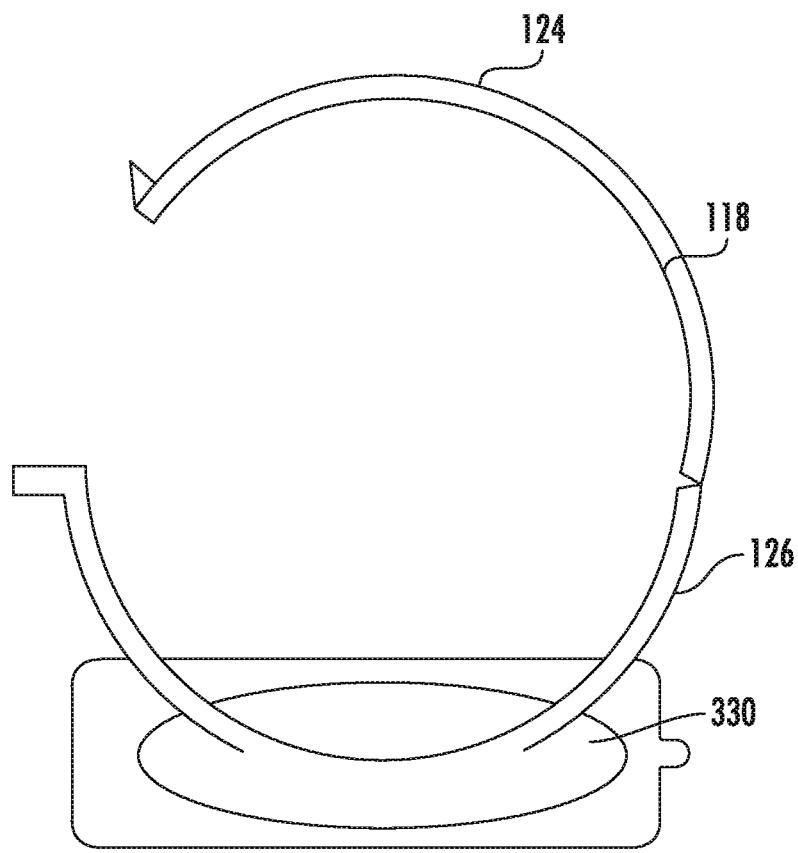
FIG. 15 is a front view of a clip secured to an adhesive clip, according to another embodiment of the present invention.
Figure 16:
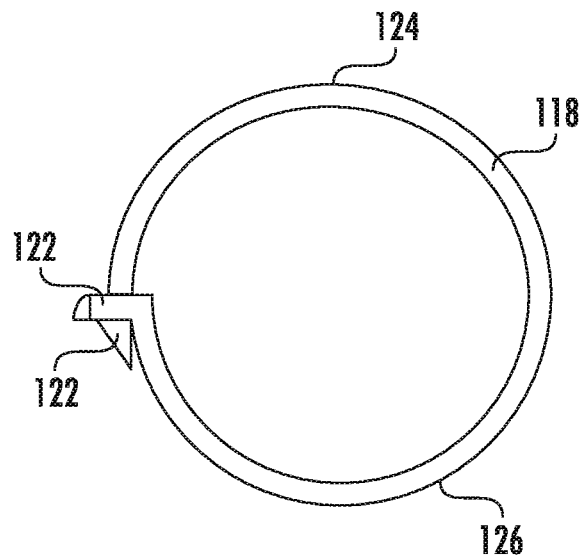
FIG. 16 is a front view of a clip, according to another embodiment of the present invention.

Referring to FIGS. 15 and 16, according to another embodiment of the present invention, the clip 118 can have a first 124 and a second portion 126. The second portion 126 is secured to the adhesive strip 330. The first portion 124 can be opened to receive an oxygen tube (shown in FIG. 15) and closed and snap onto the second portion 126 (shown in FIG. 16) to secure an oxygen tube in place. The clip 118 is preferably made of pliable plastic material such that the first portion 124 is easily snapped into the second portion 126 and a user can manipulate (e.g., open, close, rotate, etc.) at least a portion of the clip 118 to secure the oxygen tube.

Figure 19:
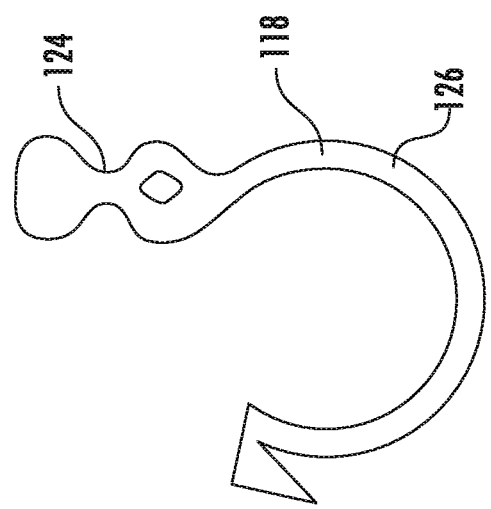
FIG. 19 is a font view of the clip of FIG. 17 in open position.
Figure 18:
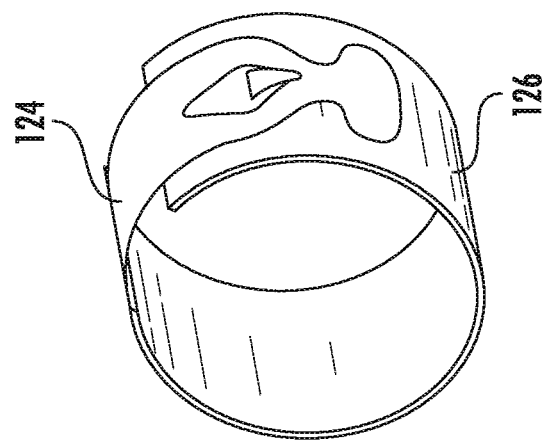
FIG. 18 is a perspective view of the clip of FIG. 17 in closed position.
Figure 17:
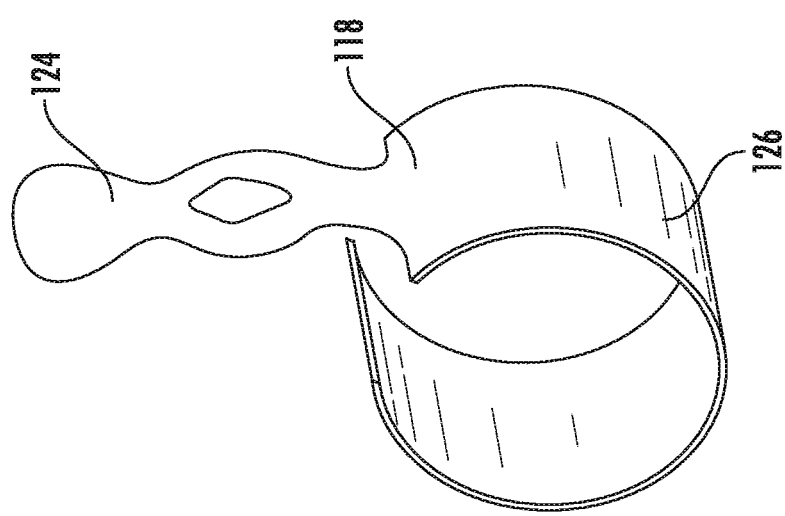
FIG. 17 is a perspective view of a clip in open position, according to another embodiment of the present invention.

Referring to FIGS. 17-19, according to another embodiment of the present invention, a first portion 124 of the clip 118 is elastic and the first portion 124 can be stretched over the oxygen tube and attached to a second portion 126 of the clip 118. The second portion 126 can be rigid and pliable.

Figure 20:
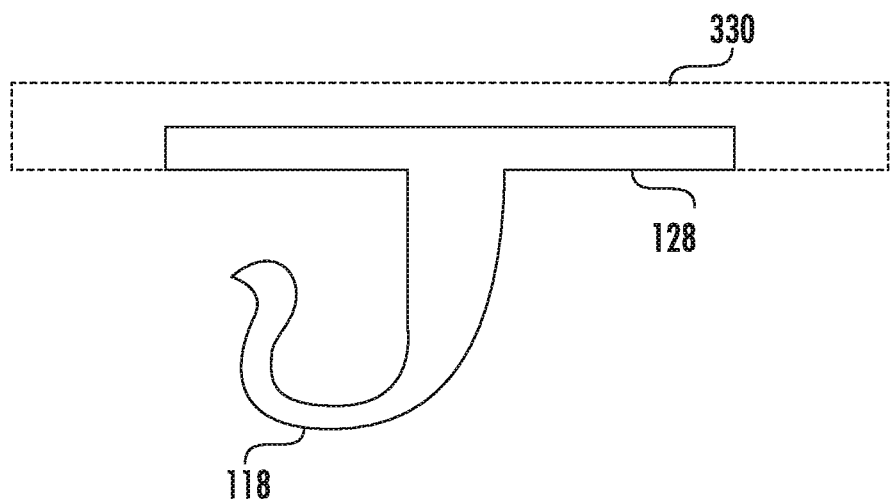
FIG. 20 is a front view of a clip as a hook in a retracted position, according to one embodiment of the present invention.
Figure 21:
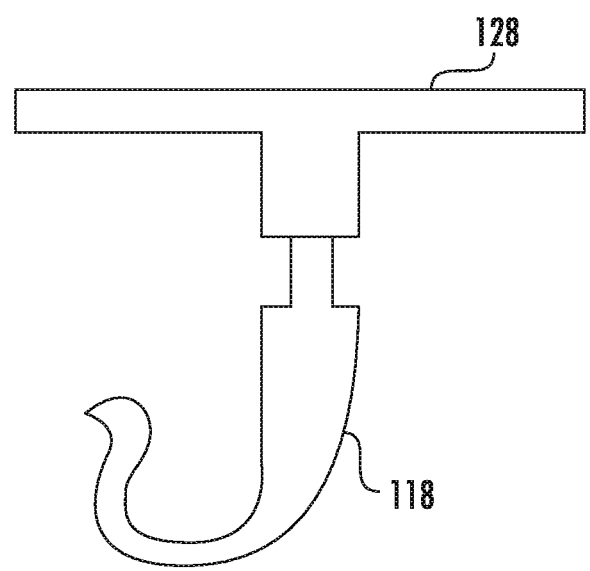
FIG. 21 is a front view of a clip as a hook in an extended position, according to another embodiment of the present invention.

According to another embodiment of the present invention, referring to FIGS. 20-21, the clip 118 is a hook. The size of the hook can vary to accommodate cannulas with different diameters. The hook can be an integral piece or assembled pieces including a support base 128 configured to be affixed to/ embedded into the adhesive strip 330. The hook can be extended as desired. For example, the hook can move up and down along an extension pole. FIG. 20 shows the hook in a retracted state and FIG. 21 shows the hook in an extended state. This would allow a patient to adjust the position and orientation of the hook to achieve a desired placement of the air delivery prongs. The hook also can be attached to the adhesive strip 330 via a hinge arrangement, a sliding arrangement, a ball and socket arrangement, Velcro, and other suitable arrangements. As such, the position and/or orientation of the hook can be adjusted via the hinge and/or ball and socket arrangement, a sliding mechanism, and the like. In the sliding mechanism, a support base having an elongated opening is attached to the adhesive strip 330 and the clip 118 can slide along the elongated opening of the support base.

The hook can be flexible or bendable for use to fit around the oxygen tube. The flexible design can enable to adapt to the oxygen tube with varying diameters. When the oxygen tube has a smaller diameter, the hook can be bended and completely enclose the oxygen tube. When the oxygen tube has a larger diameter, the hook may not completely enclose the oxygen tube, but still hold the oxygen tube in place. The hook can be made of a bendable leg (e.g., leg made of a plastic strip encased in metal) such that it can be molded around the oxygen tube and stay in place. The hook can be made of bendable straight extension leg that one can roll up and wrap around the oxygen tube.

The present invention can eliminate the need for a cannula that splits into two tubes so the oxygen can be looped around a user's ears. The adhesive strip 330 and/or the opposing legs 114 can securely attach the cannula to the user.

According to another embodiment of the present invention, referring to FIGS. 22-26, the device 200 for securing a nasal cannula to a patient includes a first adhesive strip 330 at a first end of an elongated base member 340, the first adhesive strip 330 being configured for releasable attachment to the columella of a nasal septum. The device 200 further includes a second adhesive strip 342 attached to the elongated base member 340 and configured for releasable attachment to an upper lip of the patient. The device 200 further includes a clip 118 connected to the elongated base member 340, the clip 118 having an opening configured to secure the device to an oxygen tube 102 of the nasal cannula. The first adhesive strip 330 is configured to secure the device to the columella of the patient, and the second adhesive strip 342 is configured to provide further stabilization of the device and prevent wobbling of the device on the patient, especially during sleep. The first adhesive strip 330 and the second adhesive strip 342 can vary in shape, being oval, circular, square, rectangular or the like.

In preferred embodiments of the present invention, the elongated base member 340 is flexible and conformable to the shape of the columella and/or the nasolabial angle of the individual patient. For example, the elongated base member 340 is bendable upwards or downwards, depending on patient need, so that both the first and second adhesive strips 330 and 342 can be placed properly on the patient.

The device 200 can also include an extension member 400 between the elongated base member 340 and the clip 118. This provides more spacing, making it easier to attach and remove the cannula. For example, the extension member 400 can have a telescopic feature to allow the patient to raise or lower the clip 118 as desired.

Figure 27:
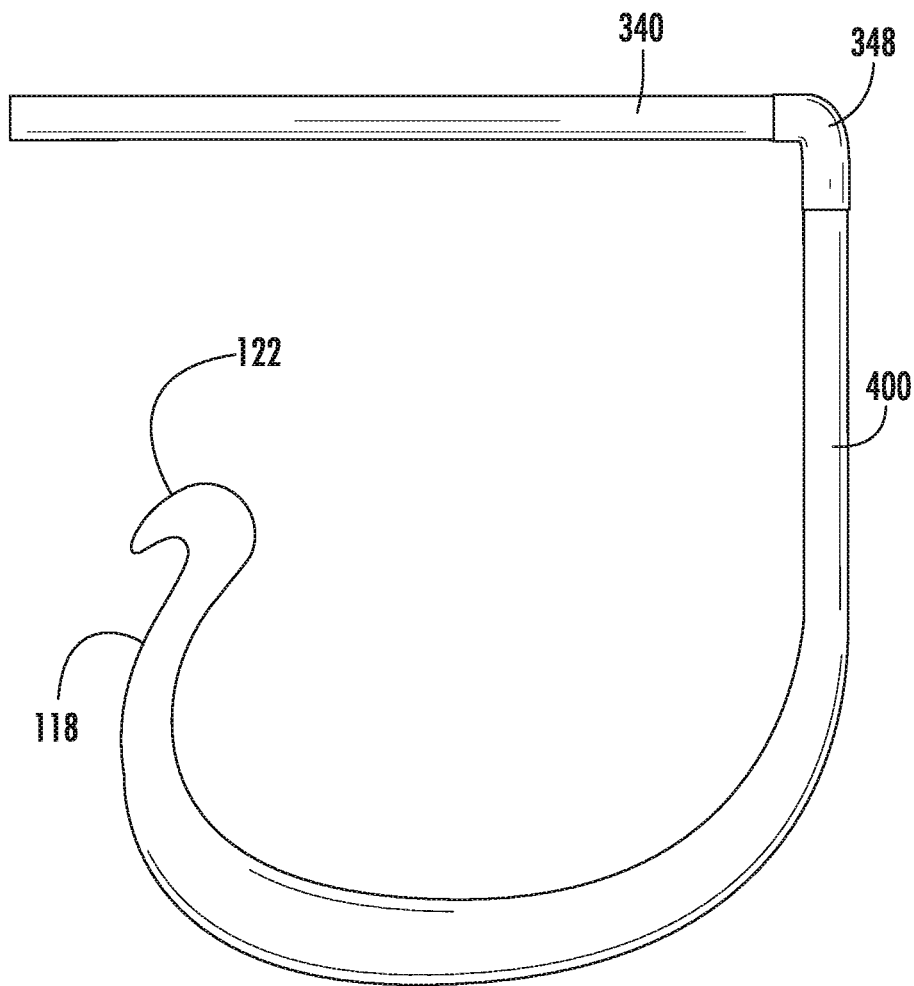
FIG. 27 is a side view of a connection between the clip and the base member of a device to secure a nasal cannula to a patient according to another embodiment of the present invention.

The clip 118 can be secured to the elongated base member 340 via a hook-and-loop-type of fastener, a magnetic type of fastener, a hinge type-type of fastener 346 (shown in FIG. 26), or a flexible connector 348 (shown in FIG. 27) made of flexible material such as rubber. The clip 118 can be permanently or releasably secured to the elongated base member 340. In the releasable attachment, the clip 118 can be easily removed and/or reattached to the elongated base member 340, for example, via attraction of magnets having opposite poles, hook-and-loop-type of fastener, a ball- and socket-type of fastener, and the like.

Figure 22:
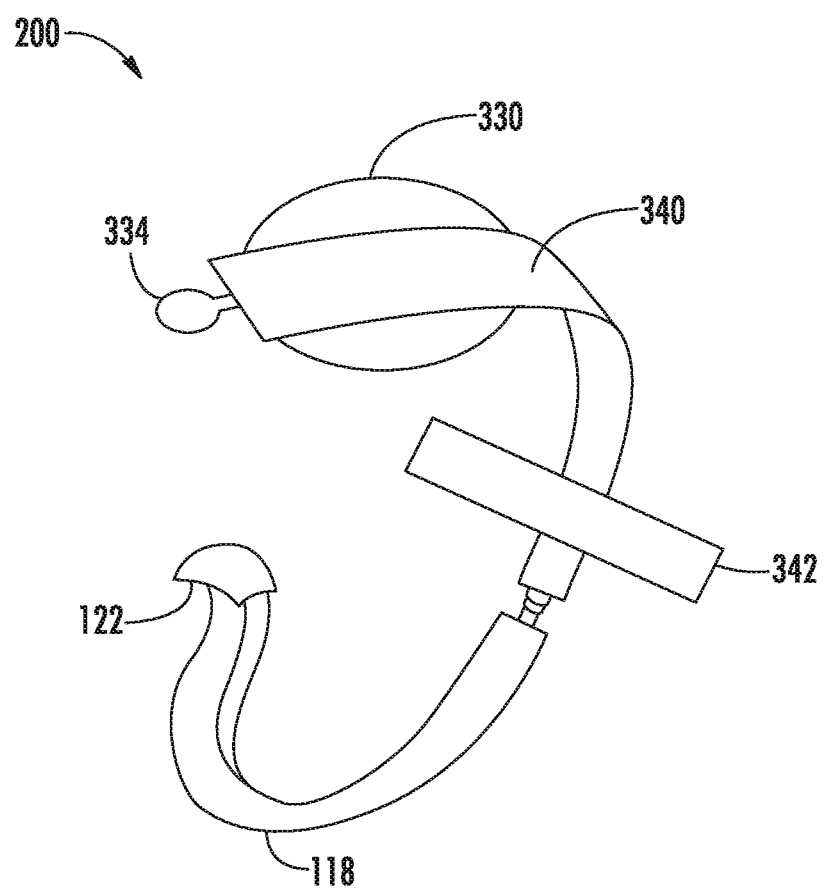
FIG. 22 is a perspective view of a device to secure a nasal cannula to a patient according to another embodiment of the present invention.

In one embodiment the present invention, the second adhesive strip 342 is positioned between the first adhesive strip 330 and the clip 118 on the elongated base member 340, as shown in FIG. 22. In a preferred embodiment, a plurality of small ridges 350 are formed on the elongated base member 340. The small ridges allows the elongated base member 340 to flex forward or backward and conform better to natural contours of a patient's columella and/or the profile between a patient's columella and upper lip. This flexibility of the elongated base member 340 can facilitate a patient to control the placement of air prongs in relation to a patient's nostrils. If a patient prefers the air prongs to be inserted further into a patient's nostrils, the patient would bend the elongated base member 340 upwards toward his columella. Conversely, if a patient prefers to have his air prongs further away from his nostrils, the patient can bend the elongated base member 340 more backwards. The flexibility of the elongated base member 340 can provide the same benefit as to the function of the extension member 400.

Figure 23:
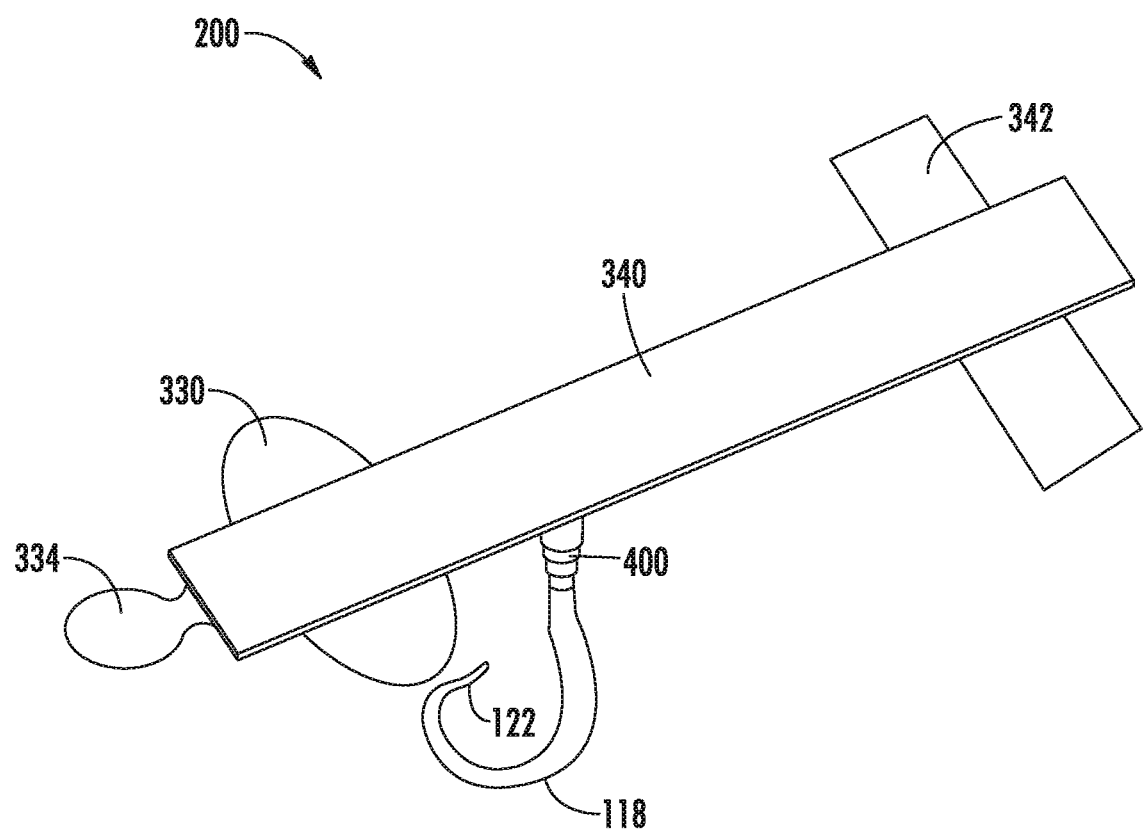
FIG. 23 is a perspective view of a device to secure a nasal cannula to a patient according to another embodiment of the present invention.
Figure 24:
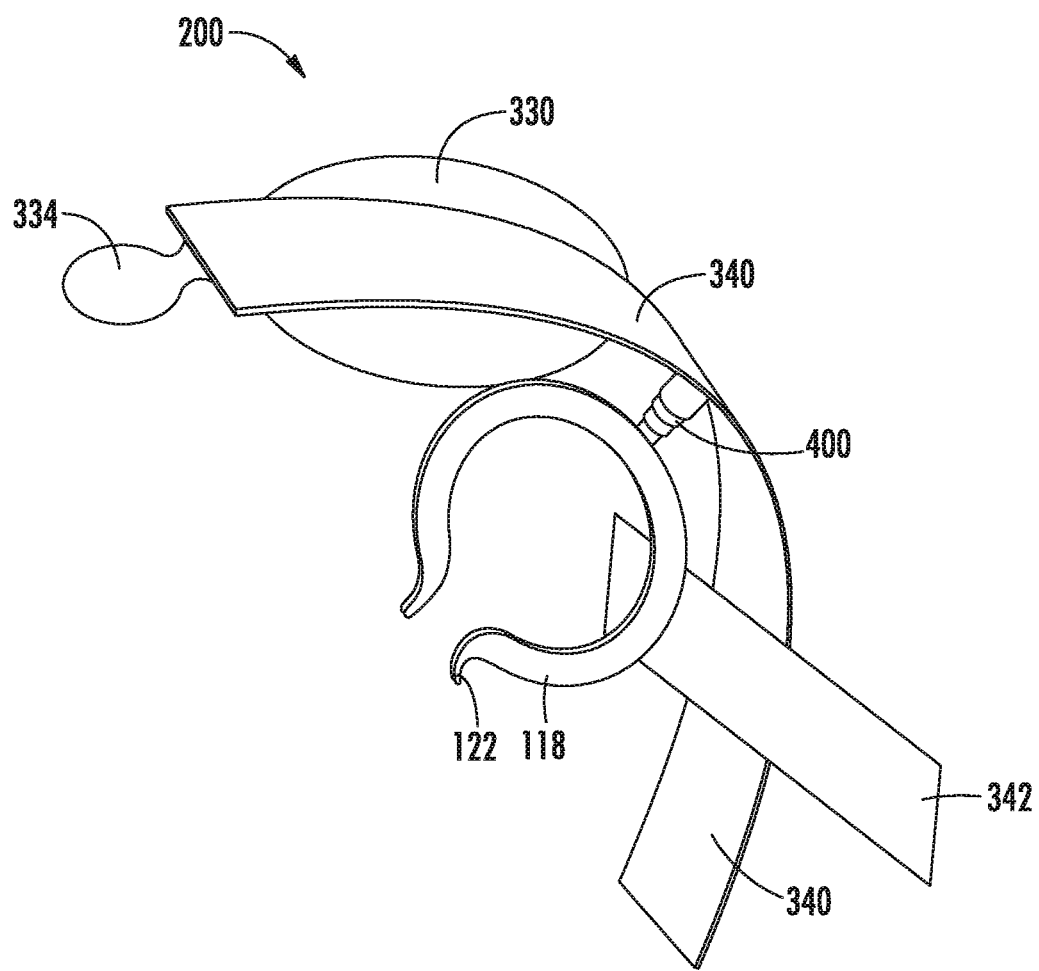
FIG. 24 is a perspective view of a device to secure a nasal cannula to a patient according to another embodiment of the present invention.
Figure 25:
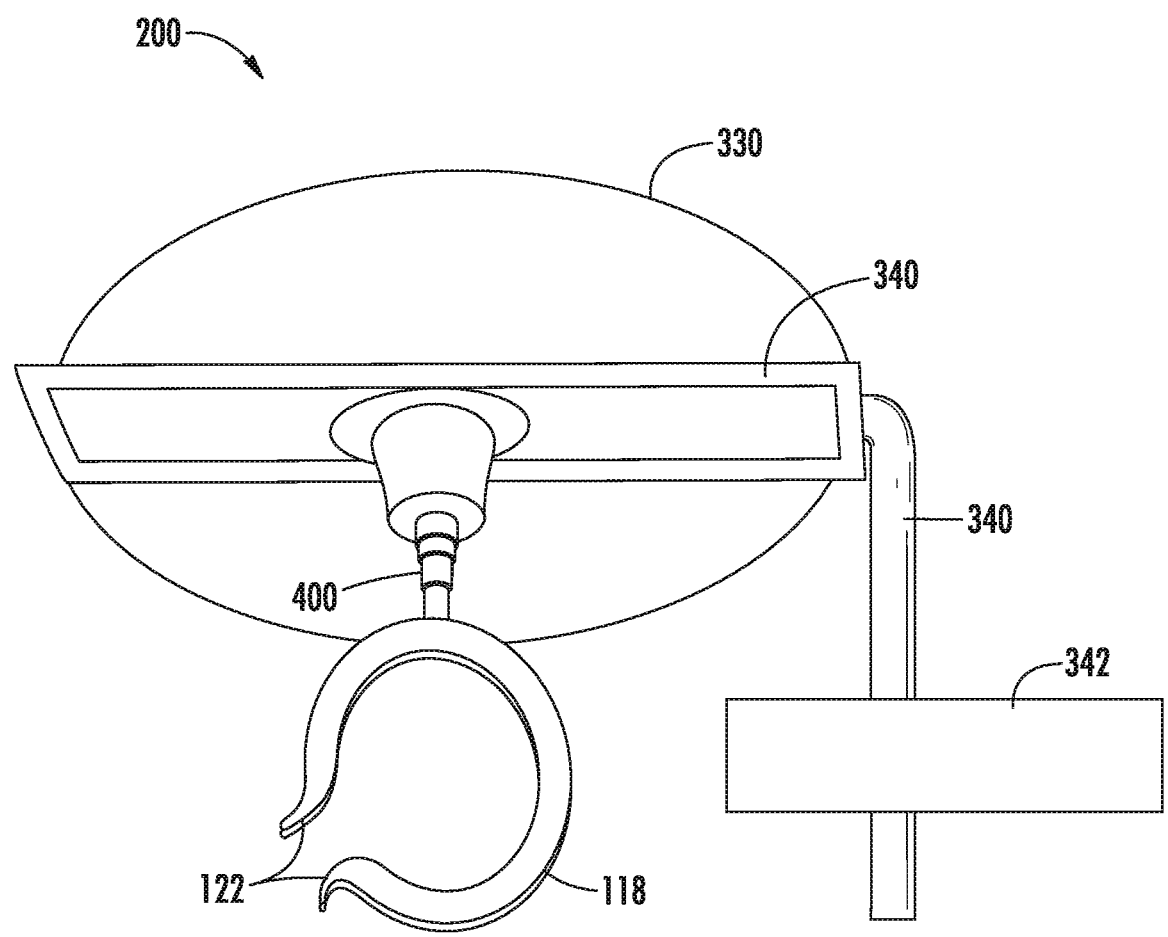
FIG. 25 is a perspective view of a device configured to secure a nasal cannula to a patient, according to another embodiment of the present invention.
Figure 26:
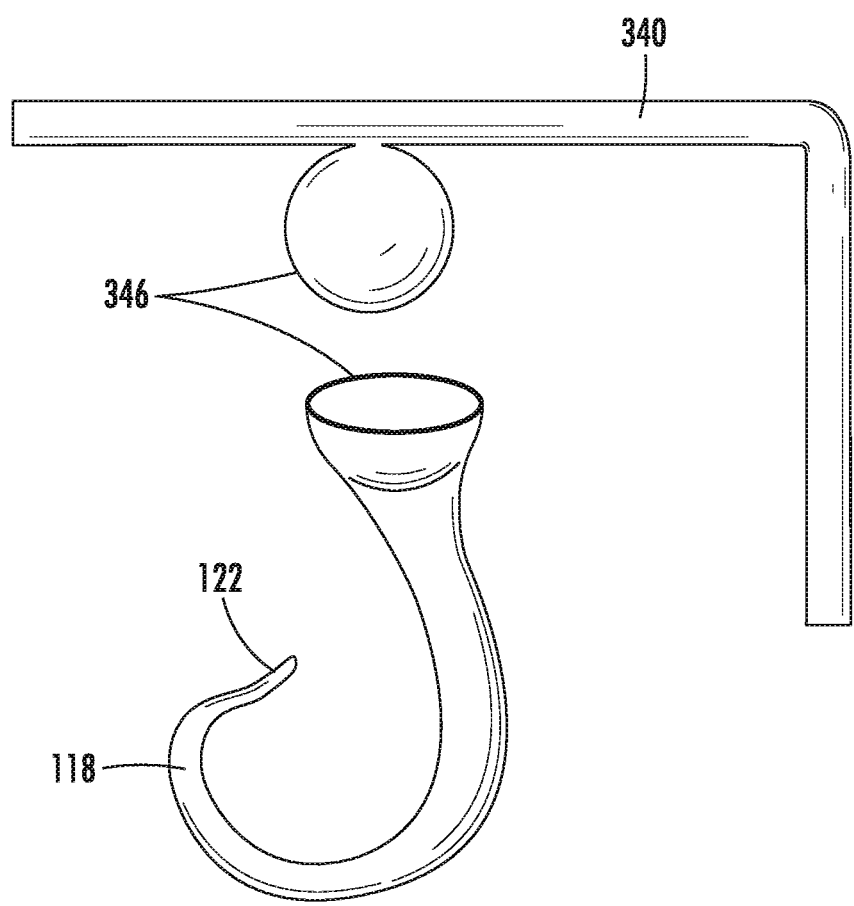
FIG. 26 is a side view of a connection between the clip and base member of a device to secure a nasal cannula to a patient according to another embodiment of the present invention.

In another embodiment of the present invention, the clip 118 is positioned between the first adhesive strip 330 and the second adhesive strip 342 on the elongated base member 340, as shown in FIGS. 23 and 24. At least a portion of the elongated base member 340 is flexible. This allows the elongated base member 400 to not only conform to the columella of a patient, but also to bend upward or downward to properly fit the air prongs near the nostrils. This embodiment may be preferable for those with larger noses.

Figure 28:
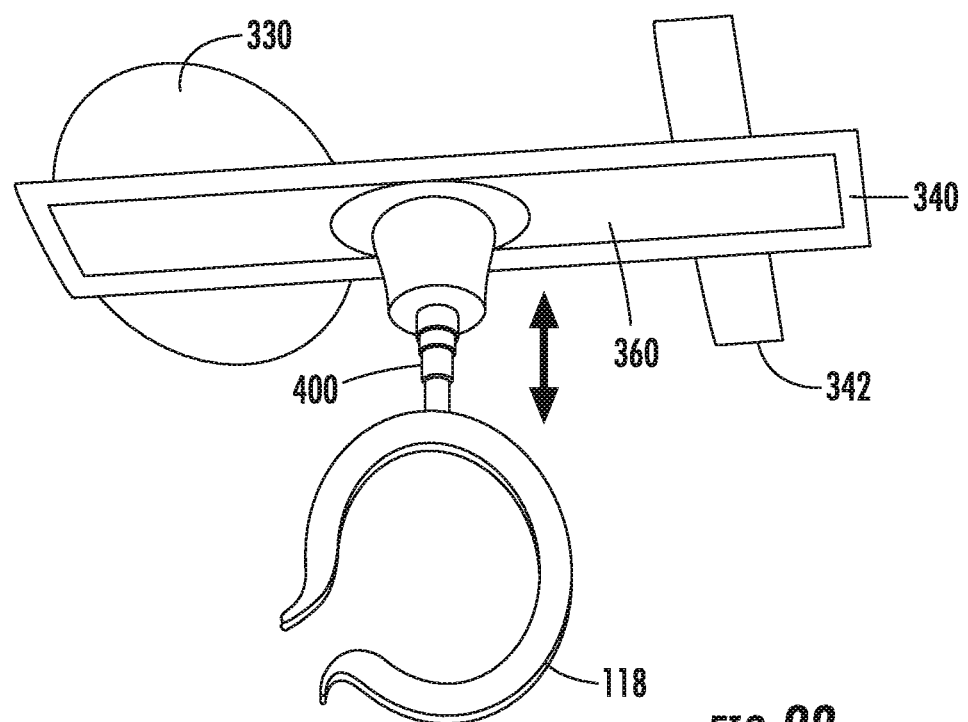
FIG. 28 is a perspective view of a device configured to secure a nasal cannula to a patient, according to another embodiment of the present invention.

Refers to FIG. 28, according to another embodiment of the present invention, the elongated base member 340 has an elongated opening 360 configured for the clip 118 to slide along the elongated member 340, and the clip 118 is slidably connected to the elongated support base member 340 and an extension member 400 (e.g., telescopic extension member) enables a patient to move the clip 118 upwards and backwards as needed by a patient. This configuration allows a patient to move the clip 118 upward, downward and/or back and forth more easily to fit the patient's needs.

Figure 29:
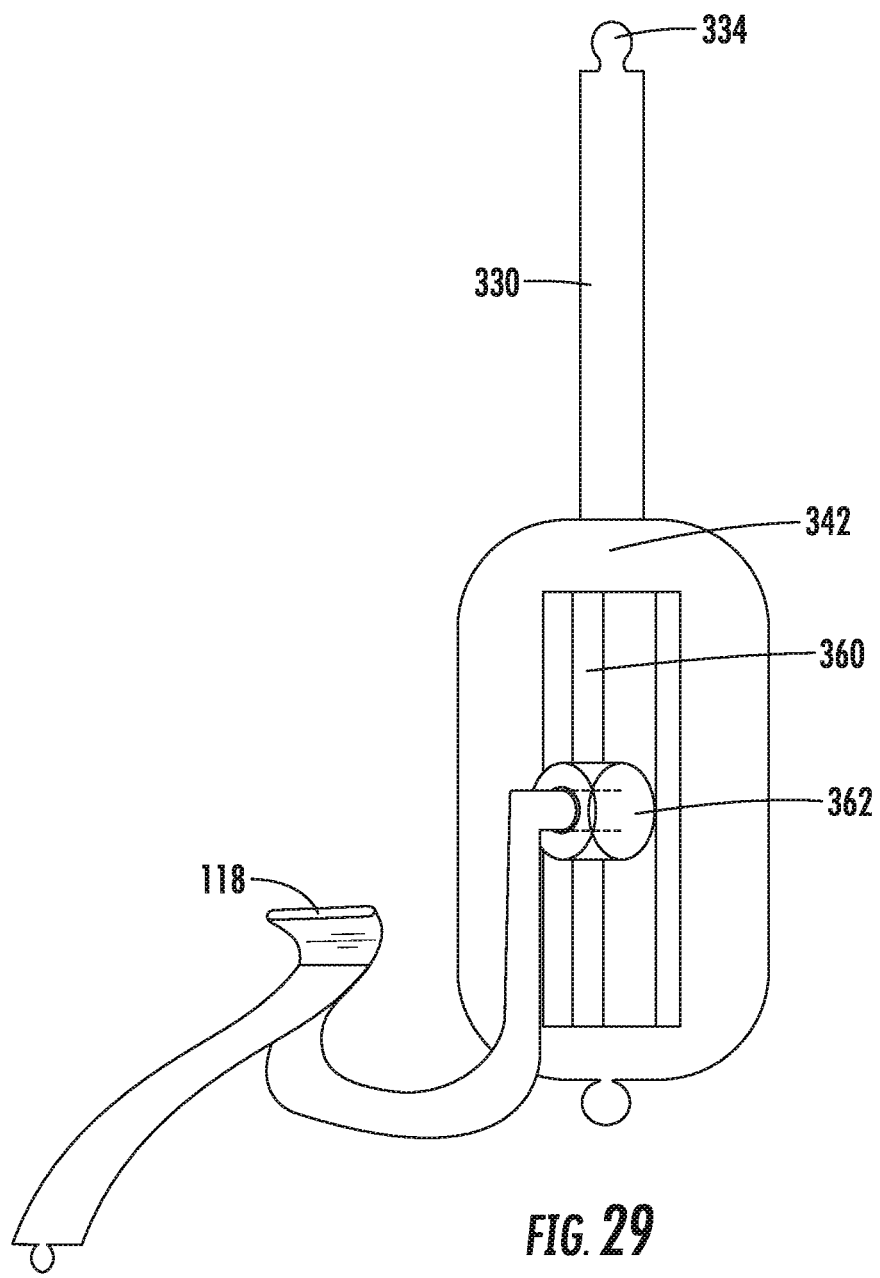
FIG. 29 is a perspective view of a device configured to secure a nasal cannula to a patient, according to another embodiment of the present invention.

Referring to FIG. 29, according to yet another embodiment of the present invention, a device for securing a nasal cannula to a patient includes a first adhesive strip 330 configured to be releasably attached to columella of a nasal septum. A second adhesive strip 342 is configured to be releasbly attached to upper lip of the patient. The second adhesive strip 342 includes an elongated opening 360. A clip 118 is slidably connected to the second adhesive strip 342 via the elongated opening 360 and the clip can slide along the elongated opening to a desired position. The clip 118 has an opening configured to secure the device to an oxygen tube of the nasal cannula. The first adhesive strip 330 can prevent the tubing or the clip 118 from making contact with the columella when the clip is positioned in close proximity to the columella. The first adhesive strip 330 can also have a pull tab 334 to facilitate removal of the device from the patient. In a preferred embodiment, the clip 118 is slidably connected to the elongated opening 360 via a flexible extension member 362 (e.g., telescopic extension member). As such, the clip 118 can slide along the elongated opening 360 and/or extend back and forth relative to the patient. This allows a patient to have total control of the placement of the cannula and its air prongs.

Alternately, the clip 118 can be attached so as not to telescope, with a similar adjustment achieved via rotating the cannula within the clip 118. The flexible extension member 362 is depicted as circular in FIG. 29, allowing it to rotate within the opening 360; however, the member 362 could have a more rectangular shape and maintain a constant angular relationship within the opening 360.

Figure 30:
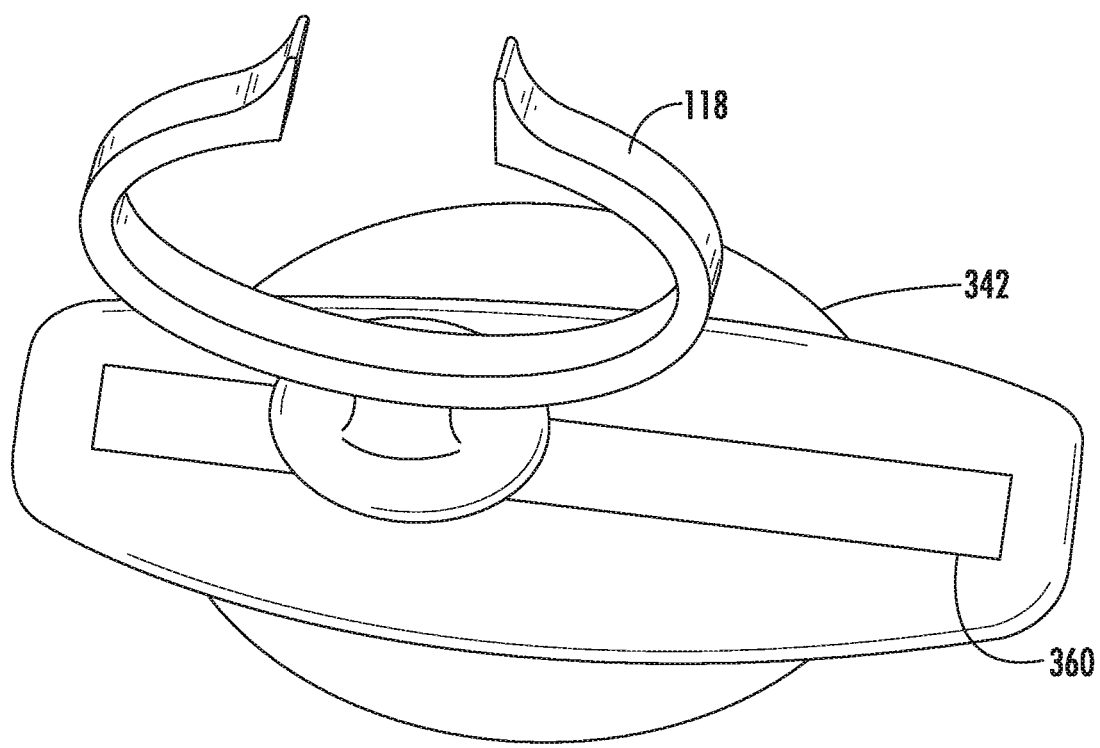
FIG. 30 is a perspective view of a device configured to secure a nasal cannula to a patient, according to another embodiment of the present invention.

Referring to FIG. 30, according to yet another embodiment of the present invention, the first adhesive strip can be omitted. Only one adhesive strip (second adhesive strip 342) is used to adhere solely to the upper lip of the patient. The adhesive strip 342 can completely or partially underlie the base of the device. Similar to FIG. 27, the base has an elongated opening 360. A clip 118 is slidably connected to the second adhesive strip 342 via the elongated opening 360 and the clip can slide along the elongated opening to a desired position. The second adhesive strip 342 can also have a pull tab to facilitate removal of the strip 342.

The clip 118 of the devices described in FIGS. 22-30 can be hook-shaped (FIGS. 22, 23, 26 and 27) or U-shaped (FIGS. 24, 25, 28, 29 and 30). The clip 118 can also include appendages 122 on the respective ends to facilitate securing the oxygen tube 102 inside the clip 118. The clip 118 can also be configured to be rotatably secured to the elongated base member 340.

Figure 31:
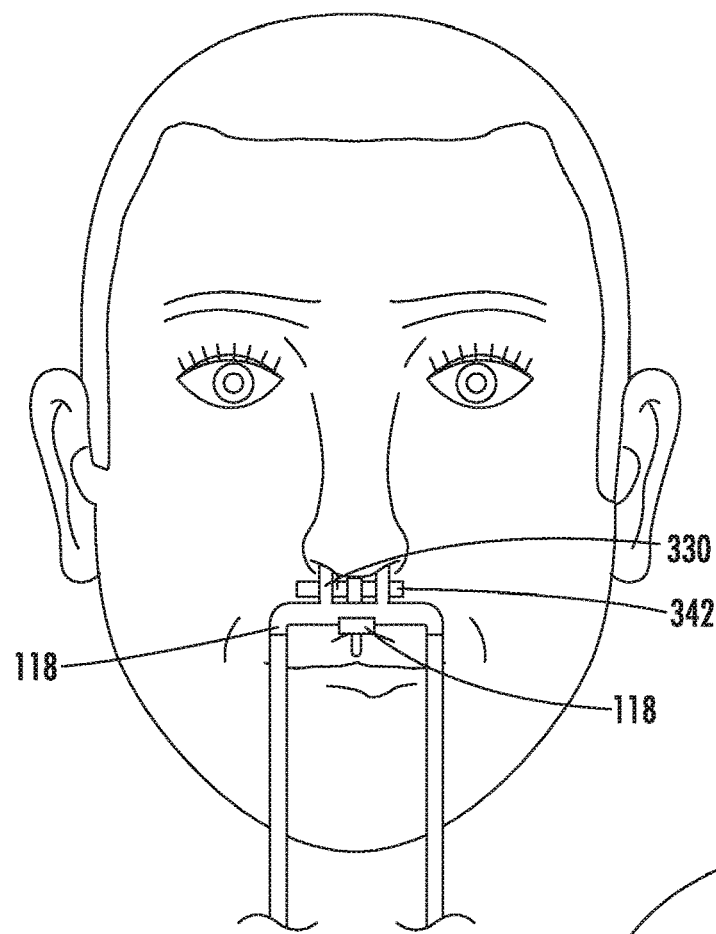
FIG. 31 is a front view of the device of FIG. 22 applied to a patient.
Figure 32:
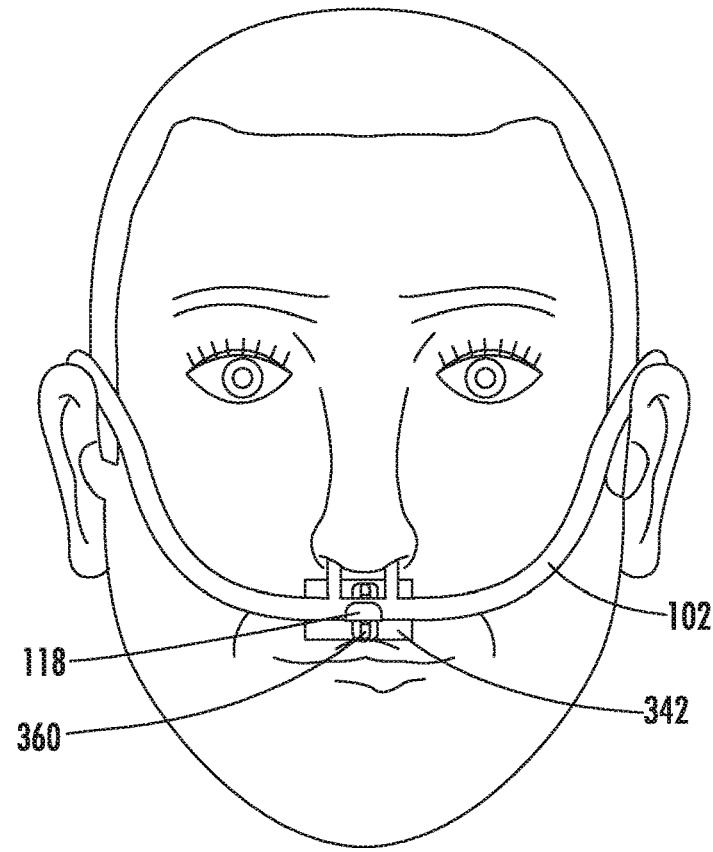
FIG. 32 is a front view of a device of FIG. 30 applied to a patient.

Referring to FIGS. 31-32, a patient wears a device shown in FIGS. 22, 23 and 30. Specifically, FIG. 31 illustrates a front view of a patient wearing the device 200 of FIG. 22. FIG. 32 illustrates a front view of a patient wearing the device 200 of FIG. 30. In this scenario, only one adhesive strip (second adhesive strip 342) is attached to the upper lip of patient.

The device 200 can be partially or entirely made out of the plastic, nylon, medical grade tape, or other suitable flexibly materials. For example, the clip 118 is can be made out of more rigid plastic material, and the elongated base member 340 and/or the extension member 400 can be made out of thinner and more flexible material. Preferably, a connection portion (e.g., connector 348 of FIG. 27) between the clip 118 and the elongated base member 340 can be more flexible than other part of the device in order to conform to the nasolabial angle of individual patient.

A method of securing an oxygen tube to a patient using a nasal cannula attachment device (device 200) includes securing the oxygen tube to the clip of the device. The first adhesive strip (e.g., first adhesive strip 330) is attached to the columella of the nasal septum. When the device does not have the first adhesive strip, the second adhesive strip 342 is attached to the upper lip surface of the patient. The device 200 can further include an extension member (e.g., extension member 400) positioned between the elongated member and the clip for adjusting a distance therebetween, and a user can adjust a length of the extension member as desired. The patient can further adjust (e.g., flex forward or backward) of the flexible elongated base member 340 connecting the first and second adhesive strip in order to conform better to natural contours of a patient's columella and/or the profile between a patient's columella and upper lip.

The first adhesive strip 330 can further include a non-adhesive pull tab (e.g., non-adhesive pull tab 334) connected to the first adhesive strip 330. When removing the device from the patient, a user can hold the non-adhesive 330 pull tab 334 to remove the first adhesive strip 330 from the columella when removing the device from the patient. When the clip 118 is rotatable, a user can rotate the clip 118 relative to the elongated base member 340 such that an opening of the clip 118 is pointed at certain orientation.

Many additional modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within.

The foregoing is provided for illustrative and exemplary purposes; the present invention is not necessarily limited thereto. Rather, those skilled in the art will appreciate that various modifications, as well as adaptations to particular circumstances, are possible within the scope of the invention as herein shown and described.

What is claimed is:

1. A device for securing a nasal cannula to a patient, the device comprising:
 an adhesive strip configured to be releasbly attached to upper lip of the patient, the adhesive strip having an elongated opening;
 a clip slidably connected to the adhesive strip via the elongated opening, wherein the clip is configured to slide along the elongated opening to a desired position; and
 an extension member positioned between the adhesive strip and the clip for adjusting a distance therebetween;
 wherein the clip has an opening configured to secure the device to an oxygen tube of the nasal cannula.

* * * * *